(12) United States Patent
Shoham et al.

(10) Patent No.: US 10,583,273 B2
(45) Date of Patent: Mar. 10, 2020

(54) TIP PROPELLED DEVICE FOR MOTION THROUGH A PASSAGE

(71) Applicant: Technion Research & Development Foundation Ltd., Haifa (IL)

(72) Inventors: Moshe Shoham, Hoshaya (IL); Noam Hassidov, Bustan Hagalil (IL); Daniel Glozman, Kefar Adumin (IL)

(73) Assignee: Technion Research & Development Foundation Ltd., Haifa (IL)

( * ) Notice: Subject to any disclaimer, the term of this patent is extended or adjusted under 35 U.S.C. 154(b) by 23 days.

(21) Appl. No.: 15/936,878

(22) Filed: Mar. 27, 2018

(65) Prior Publication Data

US 2018/0289930 A1 Oct. 11, 2018

Related U.S. Application Data

(63) Continuation of application No. 14/746,660, filed on Jun. 22, 2015, now Pat. No. 9,937,326, which is a continuation of application No. 12/063,323, filed as application No. PCT/IL2006/000925 on Aug. 10, 2006, now Pat. No. 9,061,118.

(60) Provisional application No. 60/707,166, filed on Aug. 11, 2005.

(51) Int. Cl.
*A61B 1/00* (2006.01)
*A61M 25/01* (2006.01)
*A61B 1/31* (2006.01)

(52) U.S. Cl.
CPC ..... *A61M 25/0155* (2013.01); *A61B 1/00156* (2013.01); *A61M 25/0116* (2013.01); *A61M 25/0122* (2013.01); *A61B 1/31* (2013.01)

(58) Field of Classification Search
CPC .......... A61M 25/0155; A61M 25/0116; A61M 25/0122; A61M 2025/1045; A61M 2025/1047; A61M 2025/1084; A61B 1/00156; A61B 1/31; A61B 1/0008; A61B 1/00082; A61B 1/00105
See application file for complete search history.

(56) References Cited

U.S. PATENT DOCUMENTS

2007/0276181 A1* 11/2007 Terliuc ............... A61B 1/00082
600/106

* cited by examiner

*Primary Examiner* — Timothy J Neal
(74) *Attorney, Agent, or Firm* — Fish & Richardson P.C.

(57) ABSTRACT

A self-propelled device for locomotion through a lumen, comprising a set of serially arranged inflatable chambers, the end ones of which expand at least radially when inflated. Connecting passages provide fluid communication between each pair of adjacent chambers. A fluid source is attached to one of the end chambers. The connecting passages are such that the fluid inflates the chambers in a sequence, beginning with the chamber closest to the source, and ending with the chamber furthest from the source. The same sequence occurs when the chambers deflate, beginning with the chamber closest to the source, and ending with the chamber furthest from the source. The fluid source can either be a fluid supply tube, extending to a supply outside the lumen, or it can be built-in and carried by the device. The device can crawl either along the lumen wall or on an inserted guide wire.

13 Claims, 15 Drawing Sheets

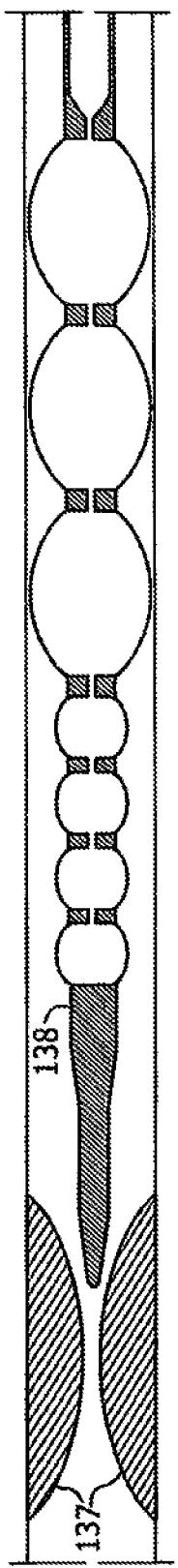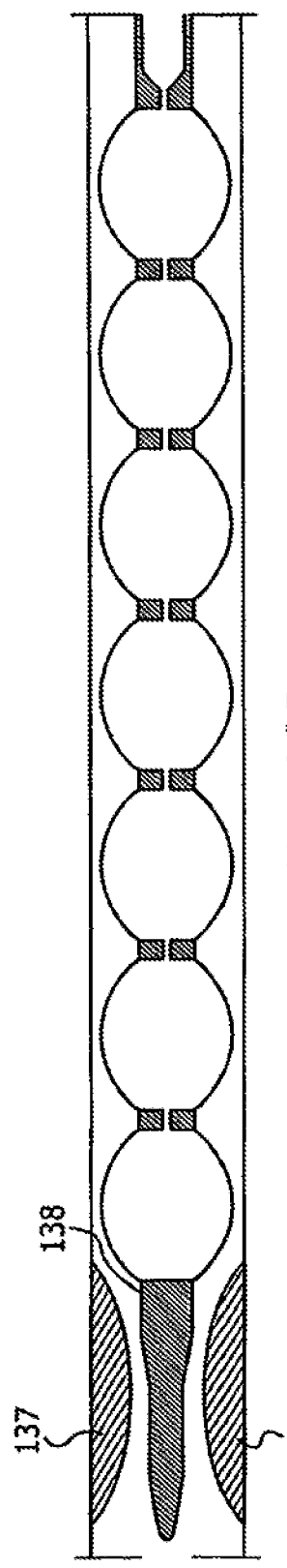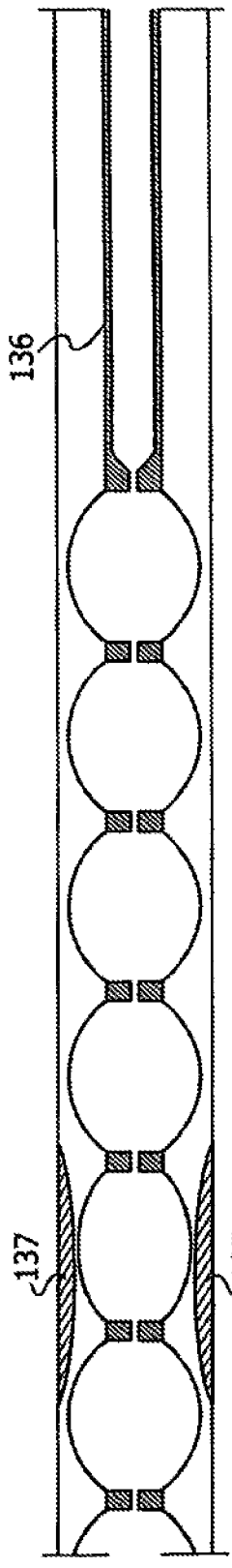

TIP PROPELLED DEVICE FOR MOTION THROUGH A PASSAGE

CROSS REFERENCE TO PRIOR APPLICATIONS

The present application is a continuation of U.S. application Ser. No. 14/746,660, filed Jun. 22, 2015 which is a continuation of U.S. application Ser. No. 12/063,323, filed Jun. 15, 2010 which is a U.S. national phase application of PCT Application No. PCT/IL2006/000925, filed Aug. 10, 2006, which claims the benefit of U.S. Provisional Application Ser. No. 60/707,166, filed Aug. 11, 2005, all of which are incorporated herein by reference. The International Application was published in English on Feb. 15, 2007 as WO 2007/017876 A2 under PCT Article 21(2).

FIELD OF THE INVENTION

The present invention relates to the field of inflatable devices capable of self-propelled motion through tubes, especially for endoscopic and vascular use.

BACKGROUND OF THE INVENTION

The ability to crawl through long, flexible, and curved tubes has long been a challenge for engineers since numerous applications can benefit from a reliable solution. This ranges from medical applications for treatment and diagnosis to sewer pipes, gas pipes and power plants.

Current solutions often contain a payload such as a camera, that is pushed from the back by a long flexible rod or wire. This is the solution currently used in most medical applications with guide wires or catheters as used to deliver diagnosis or treatment instruments to the desired position, e.g. catheterization, colonoscopy, ureteroscopy, dilating balloon, and others.

In some type of applications it is impossible to push the active head from the back because the force required would cause buckling of the long rod or wire. One of the biggest shortcomings of current endoscopes and catheters is that they are pushed into the human body manually over a curved path, thereby causing friction, and possible injuries to the inner tissue walls of the lumen.

In search for a solution, a number of locomotion types of propulsion have been developed, which pull at the distal end of the lumen rather than pushing at the proximal end. Examples in non-medical applications include crawling vehicles and spider-like robots, such as are described in U.S. Pat. Nos. 6,824,510, and 5,090,259. In medical applications the most common solution is that of the inch worm type, that advances by means of peristaltic motion, such as is described, for instance, in U.S. Pat. Nos. 6,764,441, 4,176, 662, 5,090,259, 5,662,587, 6,007,482 and 5,364,353, and in the article by P. Dario, et al., "Development and in vitro testing of a miniature robotic system for computer-assisted colonoscopy," published in Computer Aided Surgery, Vol. 4, pp. 1-14, 1999, and in the article "A Locomotive Mechanism for a Robotic Colonoscope" by Byungkyu K, et al., published in Proceedings of the IEEE/RSJ Intl. Conference on Intelligent Robots and Systems; 2003, pp. 1373-8. Another type of medical application device is described in U.S. Pat. No. 6,702,735.

Another solution is one which imitates the locomotion of the earth-worm (Annelida), that generates waves of contraction and relaxation of alternate muscle groups (longitudinal and circular muscles), causing the worm to move forward, such as is described in the article by J. Dietrich et al., entitled "Development of a peristaltically actuated device for the minimal invasive surgery with a haptic sensor array" published in Micro- and Nanostructures of Biological Systems, Halle, Shaker-Verlag, 69-88. ISBN 3-8322-2655-9. Another solution suggested uses motion hydraulically generated close to the tip, such as is described in U.S. Patent Application 2005/0033343, for "Catheter Drive" to I. Chermoni.

Most of the above described devices have the disadvantage that a number of control lines or pneumatic tubes are required to operate the device, which complicates both the control system and the physical deployment of the device within the passageway. The device described in the above-mentioned U.S. Pat. No. 5,364,353 for "Apparatus for advancing an object through a body passage" to M. T. Corfitsen et al., on the other hand, requires only one inflation tube. In this patent, there is described a device using a single bladder and an axially expandable bellows with a throttle valve between them. A tube is provided with a lumen for the supply and removal of inflation medium to the bladder and bellows. The throttling valve ensures that the inflation of the bladder is delayed relative to the axial expansion of the bellows as pressure is applied to the inflation tube, and that the deflation of the bladder is delayed relative to an axial contraction of the bellows as pressure is released from the inflation tube, such that the device can be advanced stepwise through, for instance, a gastrointestinal canal.

However, the device described in U.S. Pat. No. 5,364,353 has a drawback, which may make it problematic for use in real life situations. The device moves forward by means of axial expansion of the bellows section followed by radial anchoring of the bladder section against the inside of the passageway being negotiated, and then pulling forward of the bellows section and its trailing inflation tubes while the bladder is still anchored by its inflation pressure. However, during the forward creeping stage of the bellows, the applicants state that the device uses the bends in the trailing inflation tube to provide the friction and hence the resistance against which the device is pushed forward, this backward resistance preventing the inflation tube from being pushed back, and ensuring that the device tip moves forward.

However, the very same friction in the trailing tubing used as a rear anchor for the device when moving forward, will tend to prevent the device from pulling the trailing tubes forward as the bellows deflates. In order to pull the trailing tubing forward, the front bladder of the device presumably needs to grip the internal passageway strongly, which may not be desirable in some cases. In order to overcome reliance on the rearward friction as described in U.S. Pat. No. 5,364,353, such a device should therefore have some additional mechanism that anchors the device in place during the inflation phase.

Most of the above described devices therefore appear to have various disadvantages which limit their usefulness in one aspect or another, such that there is need for a new, distally propelled catheter head which can operate simply, over long tracts of internal passages, and without causing undue damage to the inner walls of the passages.

The disclosures of each of the publications mentioned in this section and in other sections of this application, are hereby incorporated by reference, each in its entirety.

SUMMARY OF THE INVENTION

The present invention seeks to provide a new method and device for self-propulsion along internal passageways, having a simple control system requiring only a single inflation and deflation cycle to propel the device. The device utilizes the dynamic behavior of fluid connected inflated balloons, whereby a time delay in the passage of inflating fluid from rearmost to foremost balloon is utilized to inflate the balloons in sequence beginning with the rearmost, and ending with the foremost. Conversely, this same time delay ensures that deflation of the balloons also proceeds in sequence beginning with the rearmost, and ending with the foremost. The device of the present invention uses a series of inflatable chambers to make up the traction unit, with the device sequentially gripping preferably the inside wall of the passageway with the chamber or chambers disposed at the rear or proximal end of the series while the device expands forward with inflation of the other chambers, and then gripping preferably the inside wall of the passageway with the chamber or chambers situated at the front or distal end of the series, while the device pulls up its rear end with deflation of the other chambers. By this means, no reliance is necessary on the physical situation present in the rearward tract of the passageway to provide backward frictional resistance to the trailing inflation tube, and the trailing tube can be made of a highly flexible and resilient material, such that it causes no friction or damage to the passageway being traversed. At the same time, the radial pressure which needs to be applied to the inside walls of the passageway being negotiated is minimal, since there is minimal trailing friction to overcome. Furthermore, according to further preferred embodiments of the present invention, in which the fluid source is not supplied by means of a supply tube, but is provided on board, the device is able to operate independently of its mechanical surroundings.

The device is operable with a series of only two inflatable chambers, each of which expands radially and axially when inflated, but the use of more than two chambers may have an advantage in that the radial pressure on the walls is spread out over more chambers, thus reducing the internal pressure required to anchor the relevant chambers of the device. Furthermore, the use of a larger number of chambers may enable larger payloads to be transported or pulled by the device.

The device of the present invention has a number of other advantages, either alone or in combination, over prior art devices:

(i) The device itself may be completely passive, and does not need to incorporate any actuators, engines, valves or electrical controllers on board. If required, such components may be located remotely from the device outside of the body. For those preferred embodiments where the device is autonomous, or untethered, such components may then be mounted on-board.

(ii) It may be fabricated from flexible materials only, to enable easy access to most interior cavities, and, when used in medical applications, to ensure minimum injuries and trauma to the inner tissues of the passageways of the subject.

(iii) It has only a single supply line, to enable a small, flexible and low-drag "tail". Additional tubes may be added to provide special functions, unrelated to the motive aspects of the device, such as the injection of medication at the device tip, or an X-ray opaque medium.

(iv) Lack of inflation of one or more sections, for instance due to a narrow section of the passageway, does not stop the device from functioning. The following balloons will receive the required fluid supply in that case.

(v) The propulsion system applies itself to the interior wall of the passageway or cavity over a large area and preferably covering several cells, thereby reducing the forces applied on the tissue, and reducing potential injury thereto.

(vi) The system can be constructed is such a way that keeps the inner lumen free for insertion of an endoscope, guide wires, and other surgical tools.

(vii) The balloons can be distributed along a long length of the passageway, so the propulsion effect is distributed along a long region of the passageway. This, for example, allows use in the intestine or any other long curved passageway.

(viii) The annular structure of the balloon enables the device to be designed such that its gripping pressure is applied to an inner guide wire, and the unit advances by "creeping" along this guide wire. In this way, motion can be achieved without the application of pressure to the outer wall of the passageway. This may be important, for example, to avoid applying pressure to unstable coronary plaques, or to prevent harm the inner walls.

The device according to the present invention is particularly useful in medical applications for self-propulsion of a catheter through a lumen, by its tip. It can be applied in various medical fields such as Endoscopy, Gastro-entereology, Urology, Cardiology, Cochlear implantation, sub-dural spinal applications, and others. Although the invention is generally described in this application in terms of its medical application, it is to be understood that the invention is also equally applicable to non-medical applications, where vision, accessibility or maintenance are needed in passageways, such as in industrial plant, gas pipes, power plants, tunnels, utility pipes, and the like.

There is thus provided in accordance with a preferred embodiment of the present invention, a self-propelled device for locomotion through a lumen, comprising:

(i) a set of serially arranged inflatable chambers, comprising:
 (a) at least a first and a second chamber expanding at least radially when inflated,
 (b) at least a third chamber disposed between the at least first and second chambers, the third chamber expanding at least axially when inflated, and
 (c) at least one connecting passage providing fluid communication between each pair of adjacent chambers, and (ii) a fluid source attached to one of the chambers located at a first extremity of the set of serially arranged inflatable chambers, wherein the connecting passages are adapted such that fluid from the source inflates the set of serially arranged inflatable chambers in a sequence, beginning with the inflatable chamber closest to the fluid source, and ending with the inflatable chamber furthest from the fluid source.

The fluid source may preferably comprise a fluid supply tube, which may then be adapted to be supplied with the fluid externally to the lumen, or it may comprise a pumping system attached to the device and drawing fluid from the lumen, or it may comprise a closed circuit containing the fluid and attached to the device.

In any of the above-mentioned devices, the set of serially arranged inflatable chambers also deflate in a sequence, beginning with the inflatable chamber closest to the supply tube and ending with the inflatable chamber furthest from the supply tube, when the fluid flows out of the set of serially arranged inflatable chambers.

Furthermore, the at least first and second chambers may also preferably expand axially when inflated, and the at least third chamber may also preferably expand radially when inflated.

In accordance with yet another preferred embodiment of the present invention, in any of the above-described devices, at least the first and the second inflatable chambers are adapted to grip the wall of the lumen on expanding radially. Furthermore, the above-described devices are such that the device moves along the lumen as the chambers inflate and deflate sequentially.

There is further provided in accordance with yet another preferred embodiment of the present invention, a self-propelled device as described hereinabove, and wherein at least one of the radially inflatable chambers comprises an outer skin having at least one longitudinal section of greater rigidity than other sections of the outer skin, such that when the at least one chamber inflates, the longitudinal skin section of greater rigidity does not touch the wall of the lumen. According to another preferred embodiment of the present invention, the at least one longitudinal skin section is disposed asymmetrically around the circumference of the axis of the chamber, such that when the chamber inflates, it generates a bend in the axis of the set of serially arranged inflatable chambers.

In accordance with still another preferred embodiment of the present invention, there is provided a self-propelled device according to any of the above described embodiments, and further comprising at least one tubular chamber disposed between the fluid source and the chamber to which the fluid source is attached, and in fluid contact with both, the tubular chamber being adapted to inflate radially so as to apply pressure to the lumen walls, and a pressure operated valve which closes when a predetermined pressure higher than that required to inflate the set of chambers, is applied thereto, the pressure operated valve being disposed between the tubular chamber and the set of chambers, such that the set of chambers are isolated from pressure applied to inflate the tubular chamber.

There is further provided in accordance with still another preferred embodiment of the present invention, any of the above described self-propelled devices may further comprise a tapered tip attached to a second extremity of the set of serially arranged inflatable chambers, opposite to the first extremity attached to the fluid source, such that the tip proceeds the device as it moves along the lumen. The tapered tip may preferably be made inflatable, and in fluid connection with the inflatable chamber at the second extremity, such that the tip inflates after the inflatable chamber at the second extremity. Alternatively and preferably to the provision of a tip, any of the above described self-propelled devices may further comprise a drilling head attached to a second extremity of the set of serially arranged inflatable chambers opposite to the first extremity attached to the fluid source, such that the drilling head proceeds the device as it moves along the lumen. The drilling head is preferably powered by either the inflating fluid, or by an electric motor or by a rotating guide wire.

In accordance with yet another preferred embodiment of the present invention, there is provided a self-propelled device for locomotion through a lumen, comprising:
    (i) a set of serially arranged inflatable chambers, and
    (ii) a system supplying fluid to the set of serially arranged inflatable chambers, such that the fluid inflates the set in a serial sequence, from one end to the other end, wherein at least one of the inflatable chambers comprises an outer skin having at least one longitudinal section of greater rigidity than other sections of the outer skin, such that when the at least one chamber inflates, the rigid longitudinal skin section does not touch the wall of the lumen. In this case, according to a further preferred embodiment, all of the at least one longitudinal skin sections are disposed asymmetrically around the circumference of the axis of the chamber, such that when the at least one chamber inflates, it generates a bend in the axis of the set of serially arranged inflatable chambers.

There is further provided in accordance with yet another preferred embodiment of the present invention, a self-propelled device for locomotion through a lumen, comprising:
    (i) a set of serially arranged inflatable chambers,
    (ii) a system supplying fluid to the set of serially arranged inflatable chambers, such that the fluid inflates the set in a serial sequence, from a first end of the set to its opposite end, and (iii) an obstruction clearing tip attached to the set at the opposite end. The obstruction clearing tip may preferably be a tapered tip, or a drilling head, such that the drilling head proceeds the device as the device moves along the lumen.

In accordance with still another preferred embodiment of the present invention, there is also provided a self-propelled device for locomotion through a lumen, comprising:
    (i) a set of serially arranged inflatable chambers,
    (ii) a system supplying fluid to the set of serially arranged inflatable chambers, such that the fluid inflates the set in a serial sequence, from one end to the other end, and
    (iii) a hollow passageway running through the central region of the chambers, such that the chambers inflate annularly around the passageway. In such an embodiment, the walls of the chambers surrounding the hollow passageway may preferably have a rigidity such that the hollow passageway is not compressed by the chambers when inflated. In such a case, the central passageway may be adapted to contain a threaded element along at least part of its length, the element being unattached to the self-propelled device.

Alternatively and preferably, the walls of the chambers enclosing the hollow passageway may apply pressure to the hollow passageway when the chambers are inflated. In such a case, the central passageway may be such that the chambers grip the threaded element when inflated. Additionally, the chambers may have an external diameter such that they do not grip the lumen when inflated. In this case, the device preferably moves along the threaded element as the chambers inflate and deflate sequentially.

In either of the above two central passageway embodiments, the threaded element may preferably be any one of a guide wire, an optical fiber or a length of tubing.

There is further provided in accordance with still another preferred embodiment of the present invention, a method of characterizing parameters relating to the walls of a lumen using any of the above described self-propelled devices, comprising the steps of:
    (i) inserting the device into the lumen,
    (ii) monitoring the supply pressure of the fluid as the chambers inflate sequentially,
    (iii) determining which chamber of the set is being inflated as a function of time by observing changes occurring in the supply pressure,
    (iv) monitoring the fluid flow into the set of chambers, such that the inflation volume of each chamber is known by use of the results of step (iii), and
    (v) determining the internal diameter of the lumen at the position of each chamber from the inflation volume determined in step (iv).

This method may also preferably comprise the additional step of correlating the inflation pressure build-up and the flow rate into each chamber with predetermined relationships between the measurements and the wall compliance, such that the wall compliance of the lumen at the location of each chamber may be determined.

In accordance with a further preferred embodiment of the present invention, there is also provided a method of inserting a guide wire through a lumen, using one of the above-described devices having a hollow passageway running through the central region of the chambers, comprising the steps of:

(i) inserting the guide wire a predetermined distance into the lumen, (ii) inserting the device into the lumen such that it rides of the guide wire, (iii) moving the device through the lumen by sequential inflation of its chambers, until it envelops the tip of the guide wire, (iv) advancing the guide wire a further predetermined distance into the lumen, and (v) repeating steps (iii) and (iv) until the device reaches its target.

In such a method, the walls of at least some of the chambers surrounding the hollow passageway have a rigidity such that the hollow passageway is not compressed by the chambers when inflated, such that the device moves through the lumen by gripping the walls of the lumen. Alternatively and preferably, the walls of at least some of the chambers enclosing the hollow passageway do apply pressure to the hollow passageway when the chambers are inflated, such that the device moves through the lumen by gripping the guide wire.

There is even further provided in accordance with another preferred embodiment of the present invention a self-propelled device for locomotion through a lumen, comprising:

(i) a set of two inflatable chambers, both of which expand radially when inflated and at least one of which also expands axially when inflated;

(ii) at least one connecting passage providing fluid communication between the two chambers, and (iii) a fluid source attached to one of the chambers, wherein the at least one connecting passage is adapted such that fluid from the source inflates the two inflatable chambers in a sequence, beginning with the inflatable chamber closest to the fluid source, and ending with the inflatable chamber furthest from the fluid source.

In this preferred embodiment, the two inflatable chambers preferably also deflate in a sequence, beginning with the inflatable chamber closest to the fluid source and ending with the inflatable chamber furthest from the fluid source, when the fluid flows out of the two inflatable chambers.

In any such embodiment, the fluid source may preferably comprise a fluid supply tube, which may then be adapted to draw the fluid from a supply external to the lumen, or it may comprise a pumping system attached to the device and drawing fluid from the lumen itself, or it may comprise a closed circuit containing the fluid and attached to the device.

BRIEF DESCRIPTION OF THE DRAWINGS

The present invention will be understood and appreciated more fully from the following detailed description, taken in conjunction with the drawings in which:

FIG. 3A illustrates schematically a method of manufacturing the device of FIG. 1 using separate joined segments while

FIGS. 13A to 13D illustrate schematically an embodiment having a tapered tip able to force its way through partial blockages encountered;

DETAILED DESCRIPTION OF PREFERRED EMBODIMENTS

Figure 1:
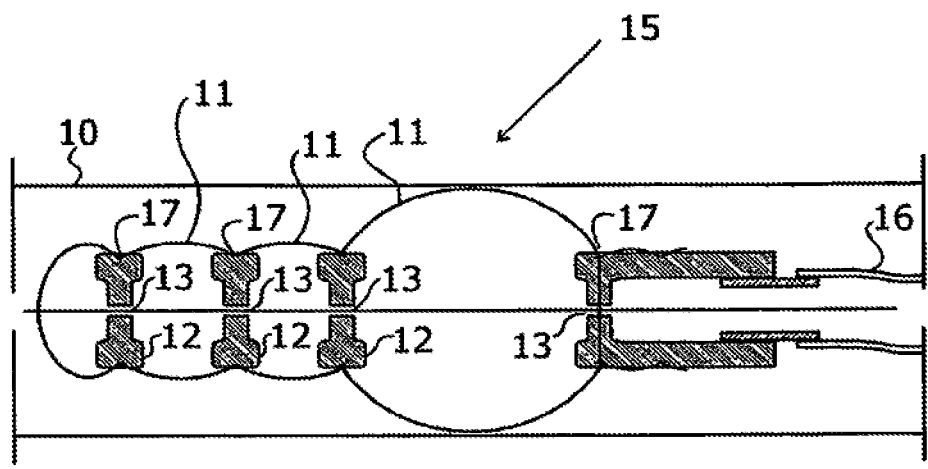
FIG. 1 illustrates schematically a tip-propelled catheter device, constructed and operative according to a first preferred embodiment of the present invention.

Reference is now made to FIG. 1, which illustrates schematically a tip-propelled catheter device 15 for traveling down a lumen 10, constructed and operative according to a first preferred embodiment of the present invention. The device preferably comprises a number of balloons 11 connected to each other by separators 12 with one or more small openings, preferably in the form of orifices 13 formed therein, such that all the balloons comprise a single volume. For ease of construction, the device can alternatively and preferably comprise a single inflatable balloon divided into separate balloon segments by separators with orifices such that the entire segmented balloon can be inflated through a single input. The balloon fabric is preferably held in place relative to the separators 12 by means of rings 17 or glued or molded to the separators. Whichever preferred construction is used, the device is connected by a single tube 16 to a fluid supply for inflating the balloons or the balloon segments. For the sake of simplicity, the operation of the device will be explained using the term balloon for each separate segment, although it is to be understood that the invention can equally be implemented using a single balloon segmented to form the separate segments. The inflation fluid used can be any one of a compatible gas or liquid.

According to a further preferred embodiment of the present invention, the fluid supply can be taken from the passageway through which the device is moving, by means of an on-board pump, and ejected thereto after use, as more fully described herein below.

Figure 2A:
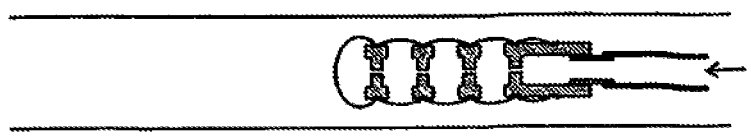
FIGS. 2A to 2I illustrates schematically how the fluid inflates the balloon cells of the device of FIG. 1 in a sequence that causes the device to move forward.
Figure 2B:
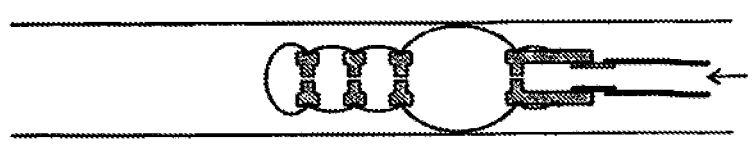
Figure 2C:
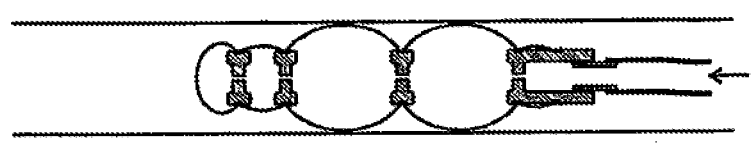
Figure 2D:
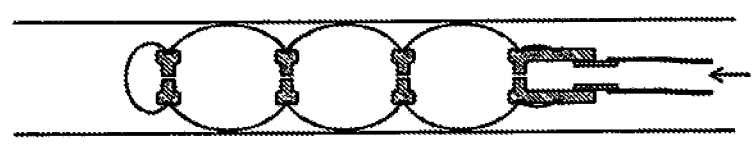
Figure 2E:
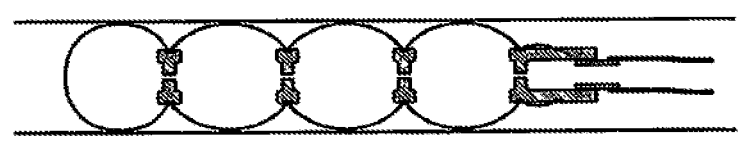
Figure 2F:
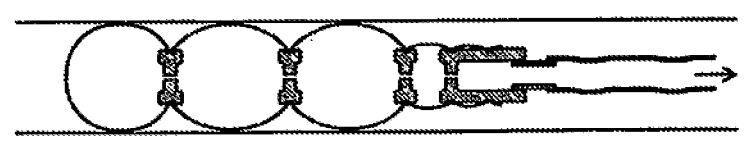
Figure 2G:
Figure 2H:
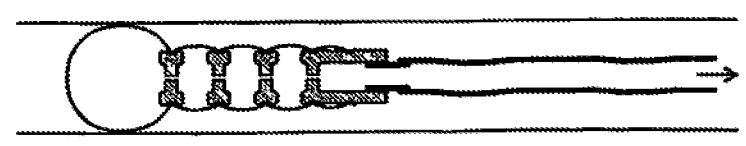
Figure 2I:
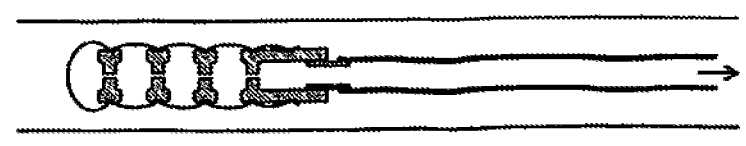

Reference is now made to FIGS. 2A to 2I which illustrates schematically how the fluid inflates the balloon cells in a sequence that causes the proximal one to inflate first, increasing its diameter as well as its length. Being inflated, it locks itself against the inside walls of the tube, but at the same time, its increase in length advances the other cells which are not fully inflated yet and hence are not locked on the inside walls of the tubes. The cell are inflated in a sequence until the distal cell locks against the inner tube walls, but at a position further along the tube than that of the un-inflated balloon distal cell initial position. This situation is reached in FIG. 2E. The timing and order of the sequence is mandated by the fluid flow dynamics through the orifices, and the dynamics of the balloon inflation. Disconnecting the supply and allowing the fluid pressure to drop at this point, or pumping out the fluid, as shown in FIG. 2F, causes the proximal cell to deflate first reducing both its length and diameter. Since the distal cell and all of the intermediary cells, are at this point still fully inflated, they are still locked against the inner walls of the tube, thus pulling the proximal cell inward as the balloon deflates and decreases its length.

The sequential motion series is repeated inducing motion of the entire device as can be seen in FIGS. 2A to 2I. The locomotion sequence is composed of two phases: inflation and deflation, with the arrows at the entrance of the inflation tube indicating the direction of fluid flow. The dynamics of the sequential inflation is as follows:

The flow through an orifice is proportional to the square root of pressure difference across the orifice, and the square of the diameter of the orifice, such that the orifice sizes can be selected to provide specific inflation dynamics.

Inflation phase: Initially, the pressure is equal in each balloon and is equal to the outside pressure, therefore the balloons are in deflated condition, as in FIG. 2A. When the pressure in the supply tube rises, the fluid begins to flow through the first orifice into the first (proximal) balloon, as in FIG. 2B. The pressure difference between the first and second balloons is now lower than the pressure difference between the supply tube and the first balloon, such that the flow rate in the second orifice is slower and the second balloon inflates more slowly than the first one. By this means, the pressure propagates in a controlled and gradual manner to the last (distal) balloon until the pressure in all the balloons is equal, as shown in FIG. 2E.

Deflation phase: Now the pressure in the supply tube is reduced to the outside pressure, or the fluid is pumped out of the inflation tube, and there is then a pressure drop between the supply line and the first balloon. The fluid begins to flow out of the first balloon, as in FIG. 2F. Again, since the pressure difference between the supply tube and the first balloon is greater than between the rest of the balloons, the first balloon deflates first, then deflates the second, and so on until the last balloon is deflated, as in FIG. 2I.

In a variation of the actuation sequence, it is possible to initiate the cycling process even before the last cell is fully deflated. In such a case there will always be a base point anchored to the passageway and hence will prevent unwanted slippage in the case of external forces. Furthermore, different orifices sizes, or different numbers of orifices, can be used between different positioned balloons to improve the locomotion and speed of the device, all according to the dynamics of the fluid flow in to, out of, and between balloons. Furthermore, the viscosity of the inflation fluid can be chosen to improve the locomotion dynamics.

Figure 3A:
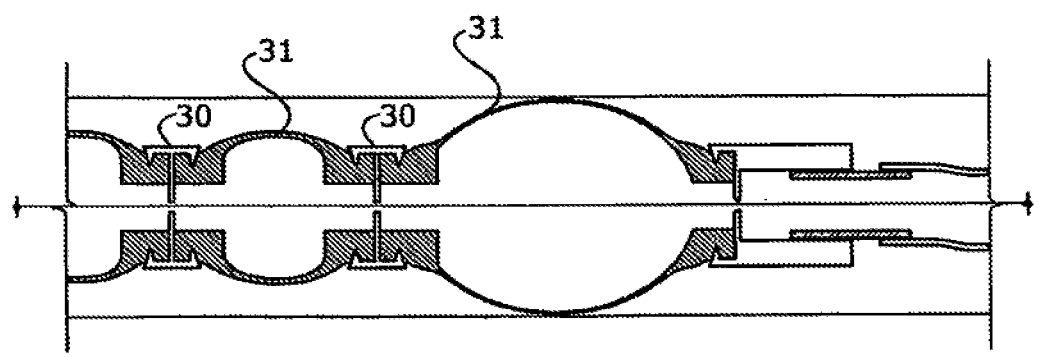

Reference is now made to FIG. 3A which illustrates schematically an alternative and preferred method of manufacturing the device, in which each section 31 is manufactured separately and sections are connected by separators 30 which act as clips for the balloon segments, with or without glue. Throughout this application, the use of the terms set or series of chambers which make up the structure of the device of the present invention, are understood to be applicable, and are thus wise claimed, whether the chambers are separate structural segments connected together, as shown in the preferred embodiment of FIG. 3A, or whether they are constructed of a single one piece structure separated into separate chambers by means of mechanical partitions, as shown in the preferred embodiment of FIG. 1.

Figure 3B:
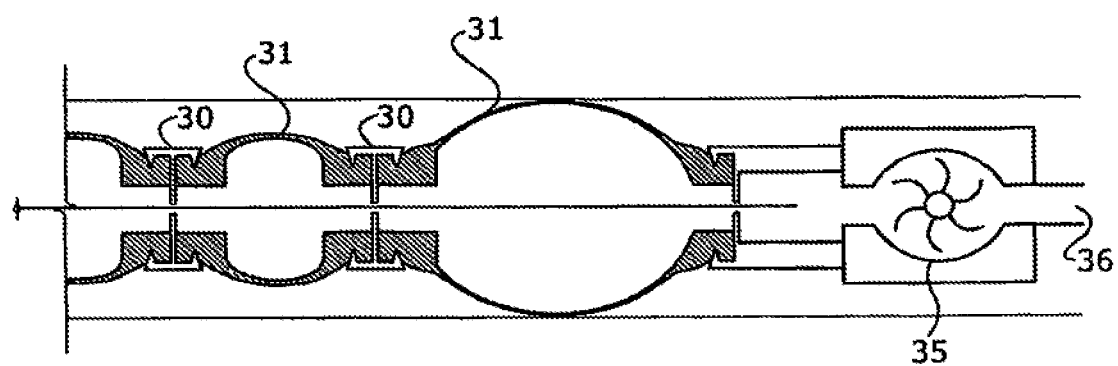
FIGS. 3B and 3C illustrate further preferred embodiments of the device of FIG. 1 in which the fluid supply system is packed on board the device, thus providing an untethered device without a trailing fluid supply line.

According to the above-described embodiments of the present invention, the supply line is attached externally to a fluid supply, and its control system, this being known as a tethered application. According to further preferred embodiments of the present invention, schematically illustrated in FIGS. 3B and 3C, the fluid actuation system can be packed on board the device, thereby obviating the need for a supply line to the outside. In the embodiment of FIG. 3B, a pump 35 is located on the device, pumping in the fluid through an opening 36 from its surrounding environment within the passageway, and expelling the fluid thereto also. If the device is operating, for example, in the vascular system, the fluid used is blood; if in a gas pipe, for example, it can use the gas to inflate and deflate the balloons; if in a regular tunnel or pipe, the fluid is the air within that tunnel or pipe. The actuation system can have an internal power source preferably in the form of a battery, or an external power source, such as an induced electromagnetic field or any other kind of induced power source. The device then moves forward unattached to any fluid supply line and solely under the control of commands transmitted to it from the outside.

Figure 3C:
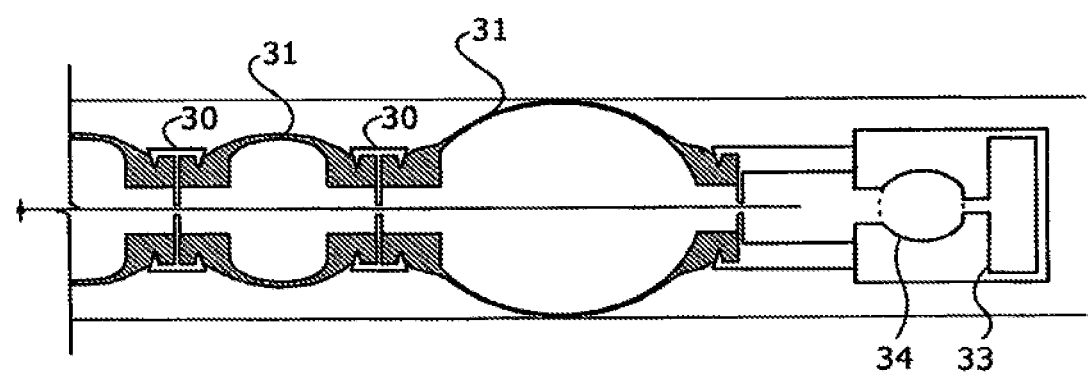

Alternatively and preferably, in a different untethered embodiment, as illustrated schematically in the embodiment of FIG. 3C, the inflating fluid is in the form of a gas, and is supplied to the inflatable balloons from an on-board reservoir 33 of the compressed gas. The inflation gas is therefore contained in a closed circuit, isolated from the fluid of the surrounding environment, and is returned to the reservoir 33 when the balloons are deflated, preferably by means of a small recycling compressor 34. The inflation fluid can then be of any suitable type of gas, independent of the fluid flowing through the passageway.

Figure 4A:
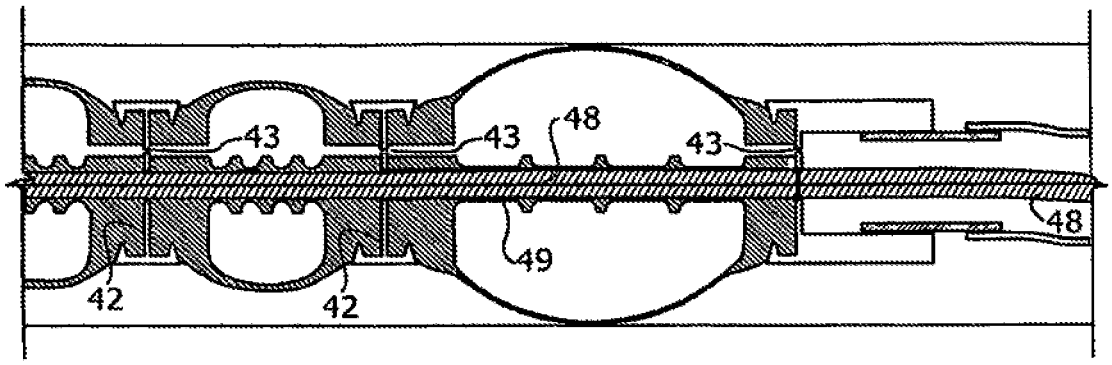
FIGS. 4A and 4B illustrate schematically a preferred embodiment of the device of FIG. 1, incorporating a passage for a central tube.
Figure 4B:
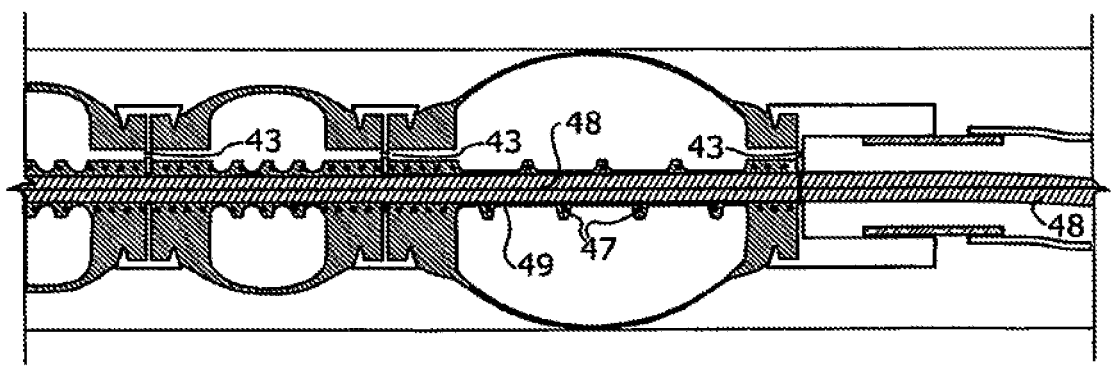

Reference is now made to FIGS. 4A and 4B which illustrate schematically a further preferred embodiment of the present invention, in which a central passage 49 has been incorporated into the device, preferably running through the central region of each of the balloons and the separators. The orifices 43 for the sequential pressure regulation are then offset in the separator walls 42. The central passage can be used for inserting an optional optical fiber, a guide wire, electronic leads to a camera mounted in the nose of the device, or similar. Although not apparent because of the scale of the drawing of FIGS. 4A and 4B, the central passage is of such a size that there is a small space between the inner surface 49 of the balloons and the internally inserted wire or other internally threaded item 48, so that the wire or other item can move freely through the device. In the embodiment of FIG. 4B, an inner spring 47 has been added to the structure to support the inner tube 49 from collapsing on the guide wire 48 or other internally threaded item, and locking the tube onto it, when the balloon is inflated. Alternatively and preferably, the central passage can be used to allow a continuous flow of blood or other vital fluid through the lumen being negotiated by the device, so that the balloons of the device do not block such flow.

FIGS. 4A and 4B describe the incorporation of a central passage for threading wire-like elements in a self-propelled locomotion device of the type of the previously mentioned embodiments of FIGS. 1 to 3 of the present invention. However, it is to be understood that the central passage described in the embodiments of FIGS. 4A and 4B, and the benefits arising therefrom, can also be advantageously incorporated in any of the prior art inflatable chamber self-propelling devices, and the present invention is meant to include also such embodiments.

Figure 5A:
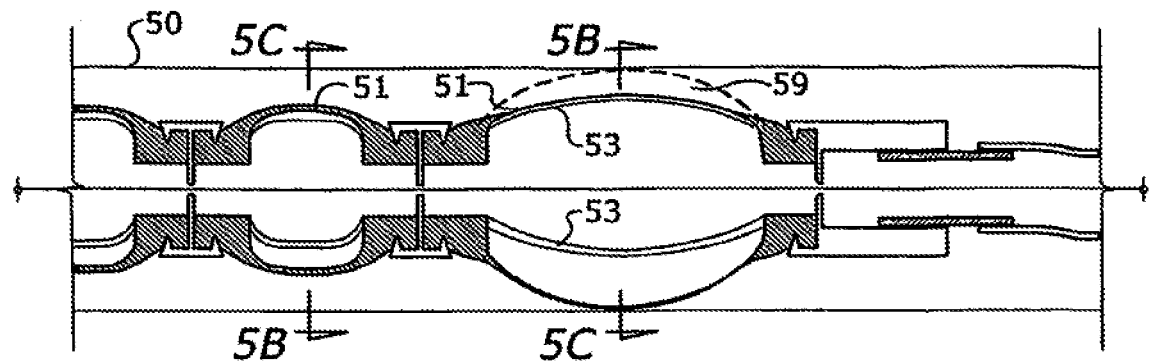
FIGS. 5A to 5D illustrate schematically a further embodiment, which enables blood or another fluid to flow around the balloons of the device.
Figure 5B:
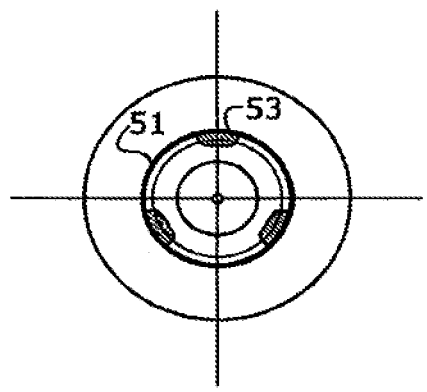
Figure 5C:
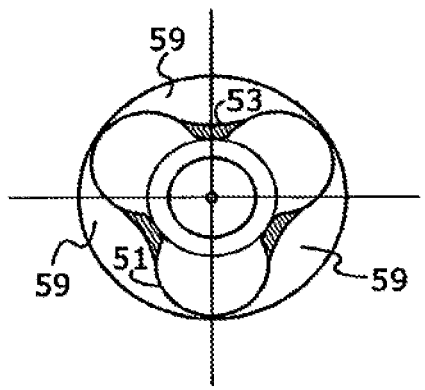
Figure 5D:
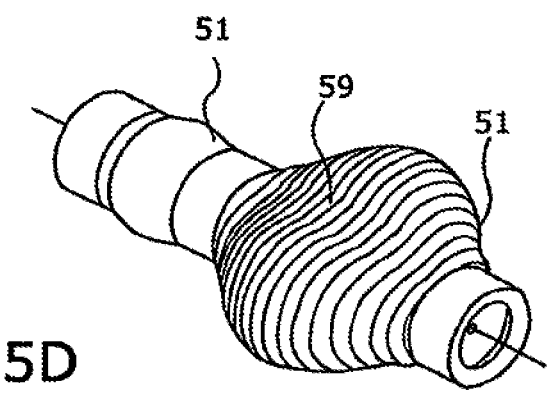

Reference is now made to FIGS. 5A to 5D which illustrate schematically a further preferred embodiment of the present invention, which enables blood or another fluid to flow around the balloons 51. This is useful in locomotion along arteries or tubes 50 where the fluid flow can not be stopped by the presence of the device, and bypasses are required. According to this embodiment, the balloons are constructed such that they do not have a circular shape when inflated. A longitudinal section of the outer skin of the balloon is constructed to be less flexible than the rest of the outer skin, preferably by the addition of longitudinal reinforcing strips 53 along the balloon length, such that the balloon does not expand to its full size, if at all, along these sections. FIG. 5B illustrates schematically a cross section of an uninflated balloon, while FIG. 5C shows an inflated balloon, showing the clear regions 59 through which the body fluid flow can continue uninterrupted. FIG. 5D shows an isometric view of the device with one balloon inflated.

FIGS. 5A to 5D describe the incorporation of a fluid bypass section in the balloons of a self-propelled locomotion device of the type of the previously mentioned embodiments of the present invention, using serial chambers with automatic inflation sequencing. However, it is to be understood that the fluid bypass section described in the embodiments of FIGS. 5A to 5D, and the benefits arising therefrom, can also be advantageously incorporated in any of the prior art inflatable chamber self-propelling devices, and the present invention is meant to include such embodiments also.

Figure 6A:
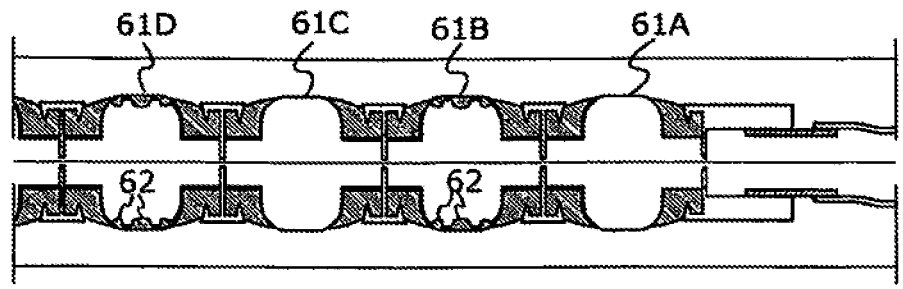
FIGS. 6A to 6C illustrate schematically an embodiment in which some of the balloons in the device inflate and expand only axially, like a bellows.
Figure 6B:
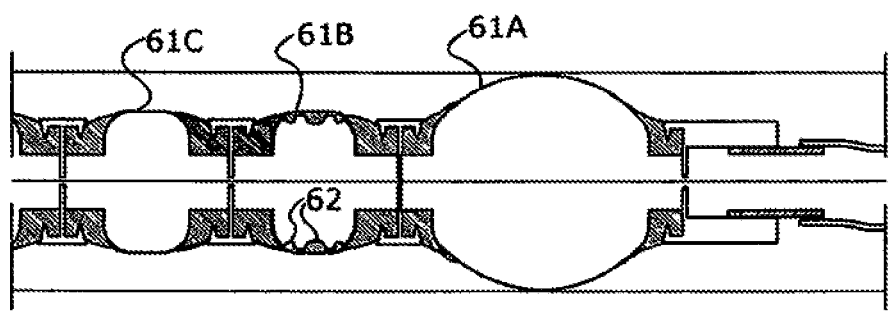
Figure 6C:
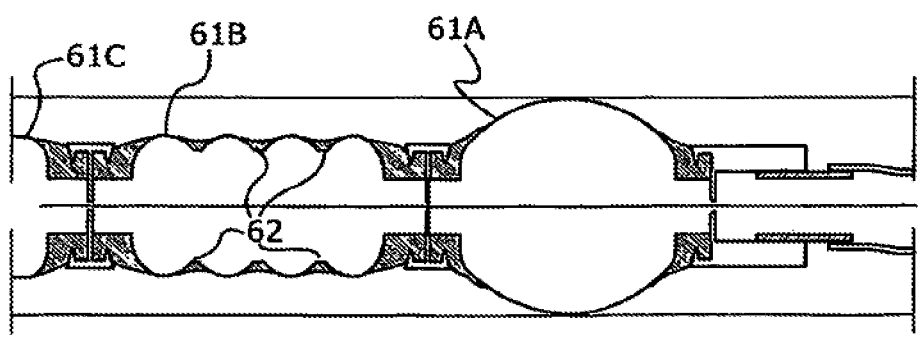

Reference is now made to FIGS. 6A to 6C which illustrate schematically a further preferred embodiment of the present invention, in which some of the balloons in the device are constructed to inflate and expand only axially, like a bellows, thereby providing a longer reach per motion cycle. In the preferred embodiment of FIG. 6A, balloons 61A and 61C are regular balloons which expand radially and axially when inflated, as shown in FIG. 6B, such that they perform the wall gripping functions of the device, while balloons 61B and 61D have reinforcing rings 62 built into their envelope, such that when they inflate, as shown in FIG. 6C, they generate significant axial expansion but little if any radial expansion.

Figure 7A:
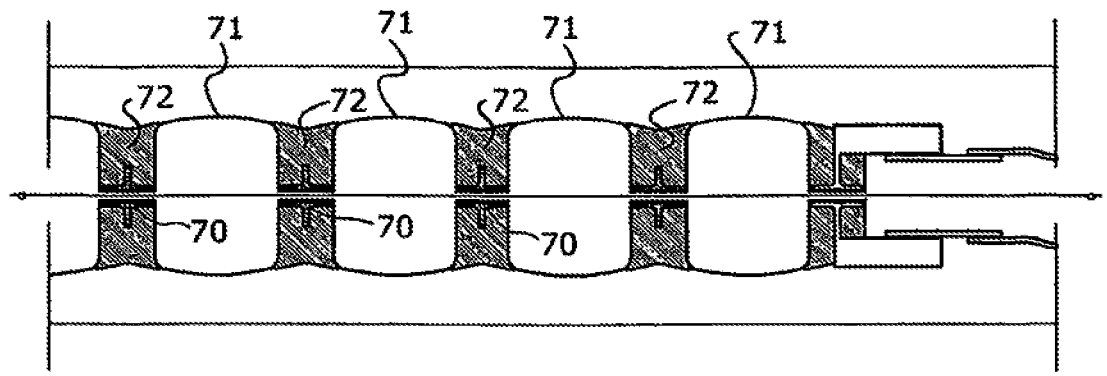
FIGS. 7A to 7C illustrate schematically an embodiment in which the device is constructed of one piece of flexible material with integral partitions and metal inter-balloon orifices.
Figure 7B:
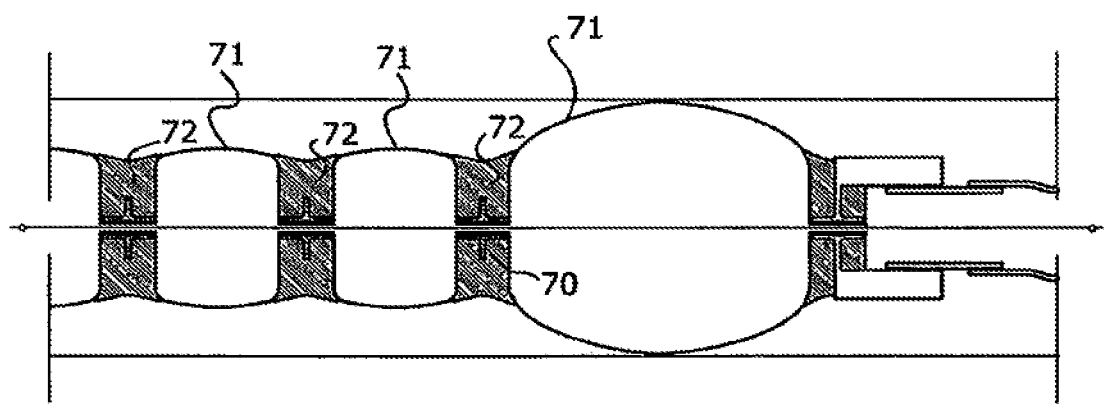
Figure 7C:
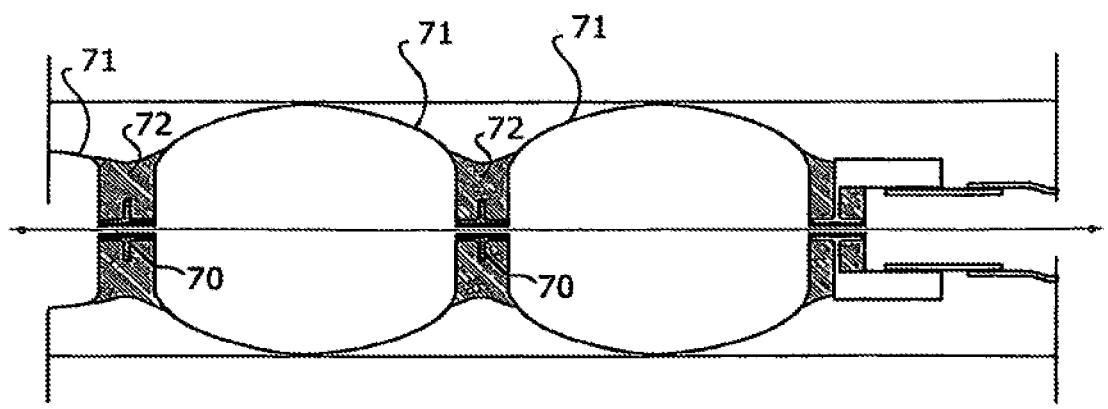

Reference is now made to FIGS. 7A to 7C which illustrate schematically a further preferred embodiment of the present invention, in which the device is constructed of one piece of flexible material with integral partitions 72 at the balloon segment dividers, and metal jet structures 70 inserted into the centers of these partitions to act as the orifices between successive balloon chambers 71. Such construction reduces the manufacturing costs of the device. Alternatively and preferably, a multiple orifice insert can be used.

Figure 8A:
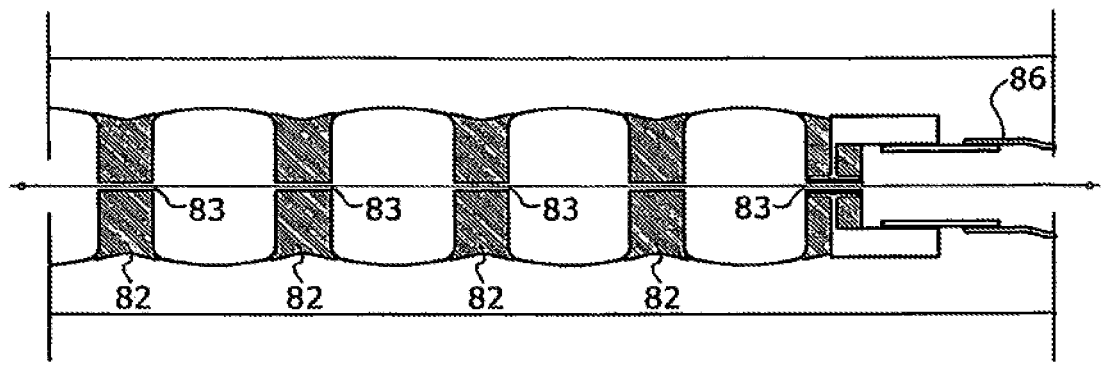
FIGS. 8A and 8B illustrate an embodiment similar to that of FIGS. 7A to 7C, but with the orifices formed in the material of the separator walls.
Figure 8B:
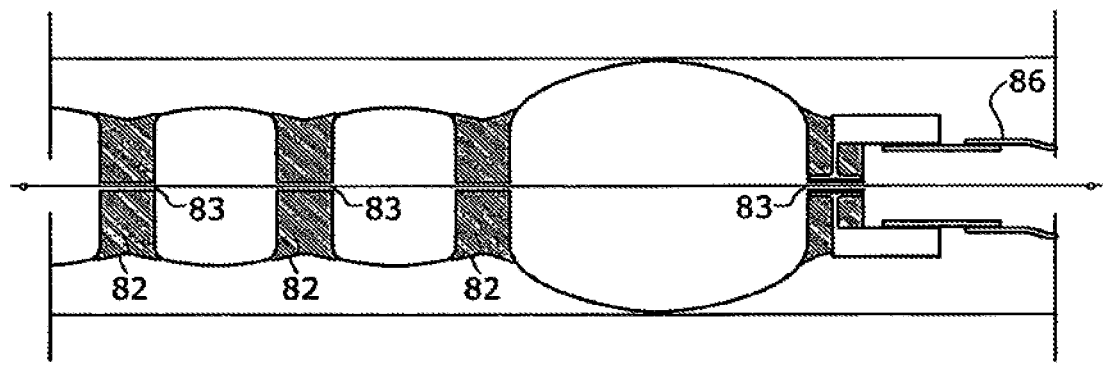

Reference is now made to FIGS. 8A and 8B which illustrate schematically a further preferred embodiment of the present invention, similar to that of FIGS. 7A to 7C, except that the orifices themselves 83 are formed in the material of the separator walls 82, thereby lowering construction costs even more. The material between sections is preferably made wider or stiffer to keep a constant orifice diameter. The supply pipe 86 can also preferably be manufactured as part of the same piece of material.

Figure 9:
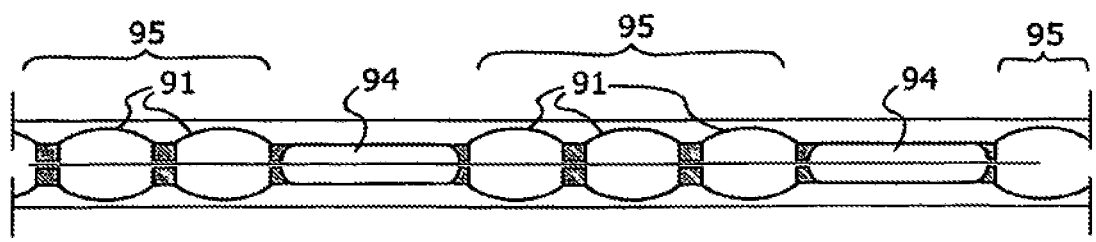
FIG. 9 illustrates schematically an embodiment showing a "Multiple Point Drive" device enabling driving forces to be deployed along the whole device, which can thus be made longer than otherwise.

Reference is now made to FIG. 9 which illustrates schematically a further preferred embodiment of the present invention, showing a "Multiple Point Drive" device. Groups 95 of driving balloons 91, or even individual driving balloons 91 can be separated with non inflatable tabular sections 94. This enables driving forces to be deployed along the whole device, resulting in a better traction and higher stroke per inflating sequence. This is very useful for moving through very long and curved passages, such as arteries or intestines or the like in medical applications. The device operates as a very long inchworm with propulsion forces along the whole body. An advantage of this embodiment, or of any embodiment using balloons over the complete length, over an embodiment using balloons only at the tip is that the crawling speed is higher since the effective stroke length is longer, and the pressure is distributed more evenly along the inner walls.

Figure 10A:
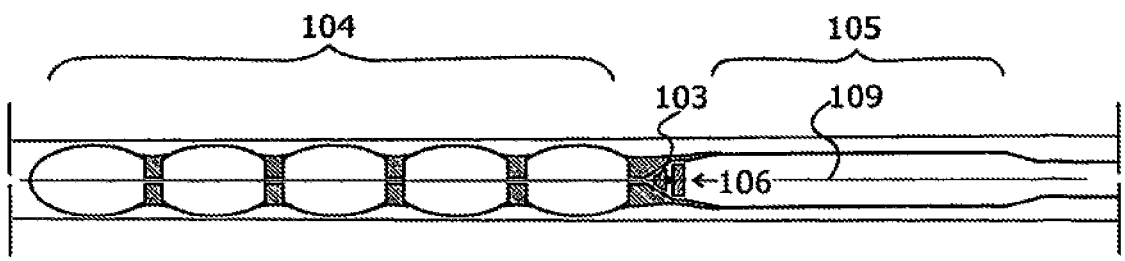
FIGS. 10A and 10B illustrate schematically an embodiment similar to that of FIG. 9, but with an inflatable straight section operative as a dilator.
Figure 10B:
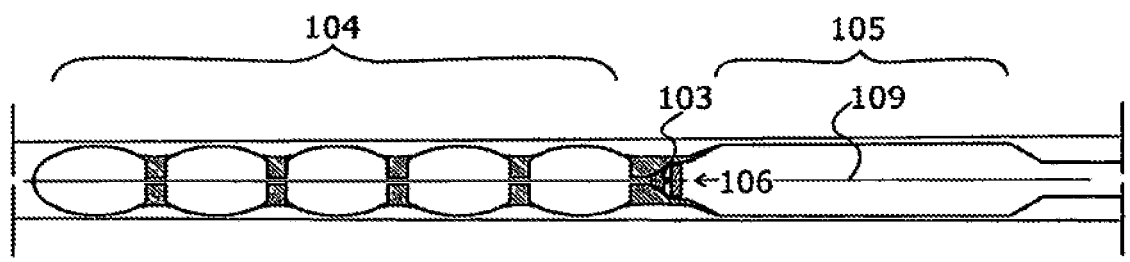

Reference is now made to FIGS. 10A and 10B which illustrate schematically a further preferred embodiment of the present invention, which has some similarities to that of FIG. 9, except that the straight sections 109 are constructed of a material that does inflate under a predefined pressure. The balloon section 104 is propelled as explained above. A pressure valve 103 is built into the entrance to the balloon section 104, and is adapted to close when the pressure 106 is raised to some higher value than that used during normal inflation operation of the balloon propulsion section 104.

This increased pressure can be used for expanding the straight chamber 109 of the device, which thus acts as a dilator section 105, available for producing therapeutic effects, without the increased inflation pressure damaging the balloon propulsion units. When the balloon propulsion units 104 have brought the device to its desired target position, the pressure 106 is increased, the valve 103 closes and the dilator 105 can be inflated with high pressure to perform its desired function. The valve 103 keeps the high pressure 106 out of the propulsion balloons. Alternatively and preferably, if the propulsion balloons 104 are made in such a way or of such a material that their inflation is limited, then no valve 103 is required.

When the therapeutic procedure is complete, pressure is lowered, the valve 103 opens again, and the device can again be operated normally. The high pressure can be used to open a partially blocked artery for example, or for expanding a stent located in its collapsed state over the section 105, or for injecting a drug from the device into the passageway being traversed, or for any other action requiring the application of a localized mechanical pressure.

The fluid supplied for propulsion can preferably be an X-Ray opaque fluid, so that it will be possible to observe the device using X-Ray imaging during insertion and propulsion.

Figure 11A:
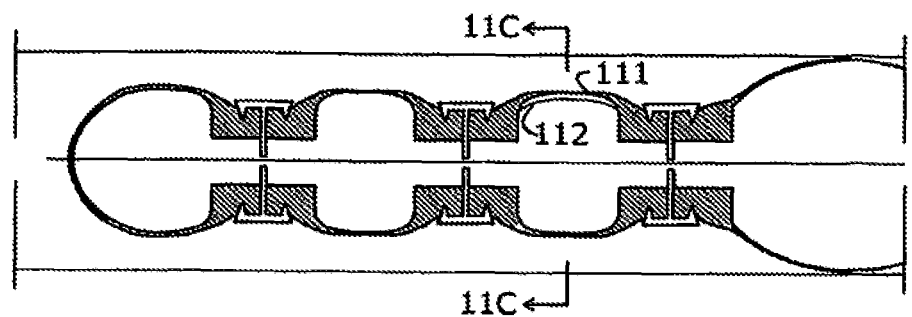
FIGS. 11A to 11C illustrate schematically an embodiment of the present invention, which is able to turn or navigate round bends in the passage being negotiated.
Figure 11B:
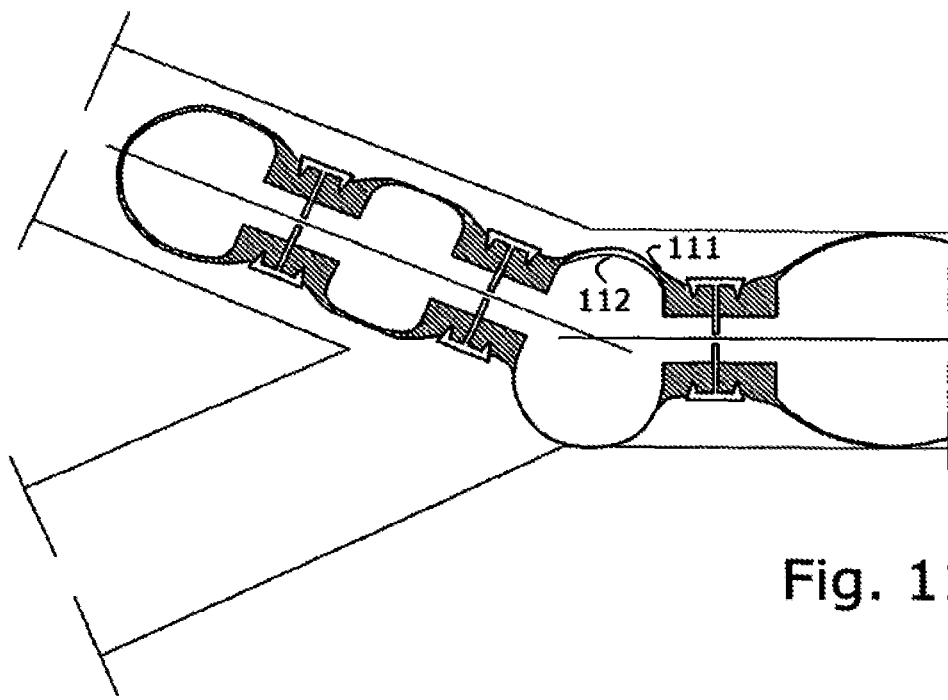
Figure 11C:
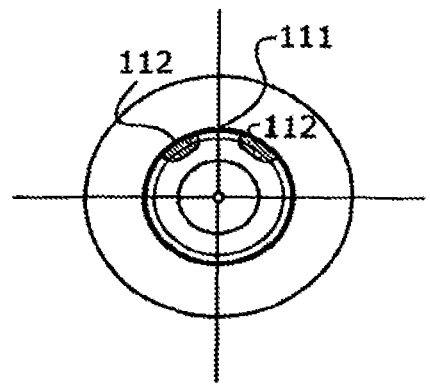

Reference is now made to FIGS. 11A to 11C which illustrate schematically a further preferred embodiment of the present invention, in which a reinforced area, preferably in the form of one or more strips 112, has been provided asymmetrically in the outer skin or wall of one or more of the balloons 111. When a balloon with such a reinforced area is inflated, the region where the reinforcement is located is not able to stretch in the same way as the other regions of the balloon, and a bending effect is generated, which can be used for turning or navigation of the device when a bend or a junction 115 in the lumen is reached, as in FIG. 11B. Such reinforcing strips can equally well be added to successive balloons of the device in order to generate a more gradual turn along the length of the device.

FIGS. 11A to 11C describe the incorporation of a reinforced section for generating a turning effect in the balloons of a self-propelled locomotion device of the type of the previously mentioned embodiments of the present invention, using serial chambers with automatic inflation sequencing. However, it is to be understood that such a reinforced section for generating a turning effect as described in the embodiments of 11A to 11C, and the benefits arising therefrom, can also be advantageously incorporated in any of the prior art inflatable chamber self-propelling devices, and the present invention is meant to include such embodiments also.

Figure 12A:
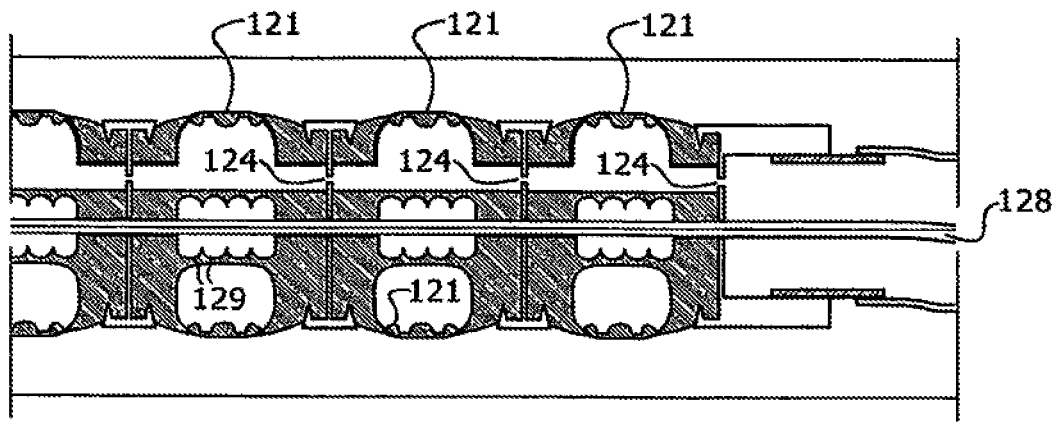
FIGS. 12A and 12B illustrate schematically an embodiment in which the locking occurs on an inside tube or guide wire.
Figure 12B:
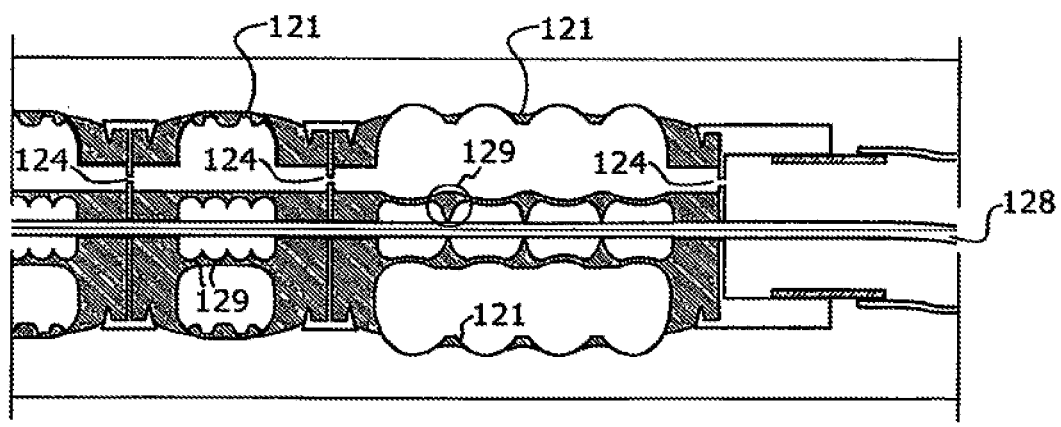

Reference is now made to FIGS. 12A and 12B which illustrate schematically a further preferred embodiment of the present invention, in which the locking occurs on an inside tube or guide wire 128. This is accomplished by making the outer surface of the balloon stiffer than the inner surface, either by using an intrinsically stiffer material for the outer skin, or, as shown in FIGS. 12A and 12B, by incorporating reinforcing ribs 121 in the outer wall. In FIG. 12A showing the balloons uninflated, though not visible in the drawing, there is a small gap between the inner passage of the balloons and the internally inserted tube or guide wire 128, so that the tube or wire or other threaded item can move freely through the uninflated device. As the balloons are inflated, the inner surface expands inwards, and eventually locks against the inner guide wire or tube, as shown in FIG. 12B. The inner surface of the balloons may preferably be fitted with fins 129, so that the balloon grips the inner tube or guide wire at narrow points, thereby increasing the pressure of the grip. Since the central axis of the device is occupied by the central tube or guide wire, the orifices 124 connecting the various balloons have to be offset from the center. Alternatively and preferably, a number of orifices can be used spread angularly around the central tube. As with the previous embodiment of FIGS. 6A to 6C, some of the sections can have essentially circular balloons, and other sections can be cylindrical axially extending balloons.

FIGS. 12A and 12B describe the incorporation of a central passage for threading wire-like elements in a self-propelled locomotion device of the type of the previously mentioned embodiments of the present invention, using serial chambers with automatic inflation sequencing. However, it is to be understood that the central passage described in the embodiments of FIGS. 12A and 12B, and the benefits arising therefrom, can also be advantageously incorporated in any of the prior art inflatable chamber self-propelling devices, and the present invention is meant to include such embodiments also.

Reference is now made to FIGS. 13A to 13C which illustrate schematically a further preferred embodiment of the present invention, in which the device is provided with a tapered tip 138 which, as the device advances through the passageway, is able to force its way through partial blockages 137 encountered. The tip partially compresses the blockage material against the wall of the passageway. Additionally, the device can preferably be fitted with a dilator section 136, as in the embodiment of FIGS. 10A and 10B, to complete the operation of clearing the partial blockage 137.

Figure 13D:
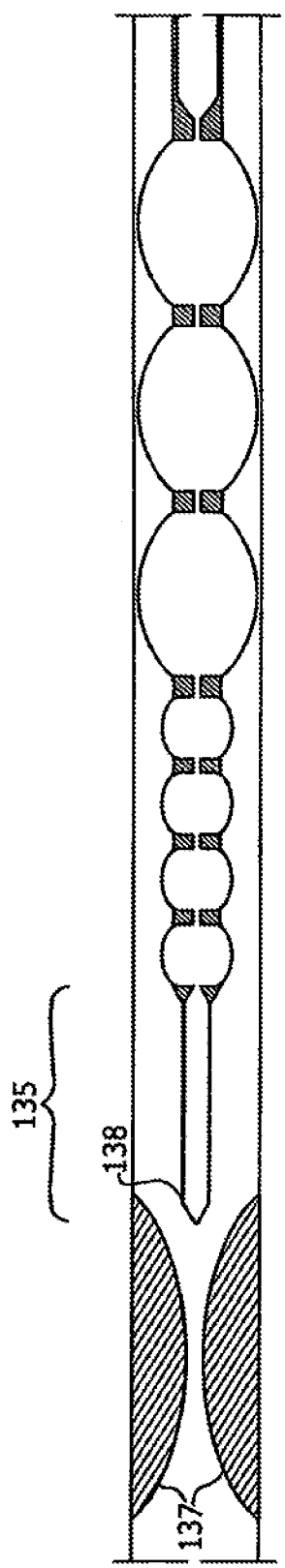

Reference is now made to FIG. 13D which illustrates schematically a further preferred embodiment of the present invention, similar to that shown in the embodiment of FIGS. 13A to 13C, but in which the tip 134 is made inflatable by means of fluid connection to the most distal balloon. The front end 135 of the tip forces its way into the blockage 137 as the device crawls forward, and when the most distal balloon has filled up, the inflatable tip head also inflates, thus packing the blockage material against the internal wall of the passageway. Since inflation of the tip occurs automatically when the distal balloon has inflated, this embodiment is simpler than that of FIGS. 10A and 10B, where additional valving and pressure monitoring is required.

According to further preferred embodiments of the present invention, in the arrangements shown in FIGS. 13A to 13D, where only some of the balloons are used for motion purpose, the rest of the balloons and the head can be used for other therapeutic purposes besides dilation.

Figure 14:
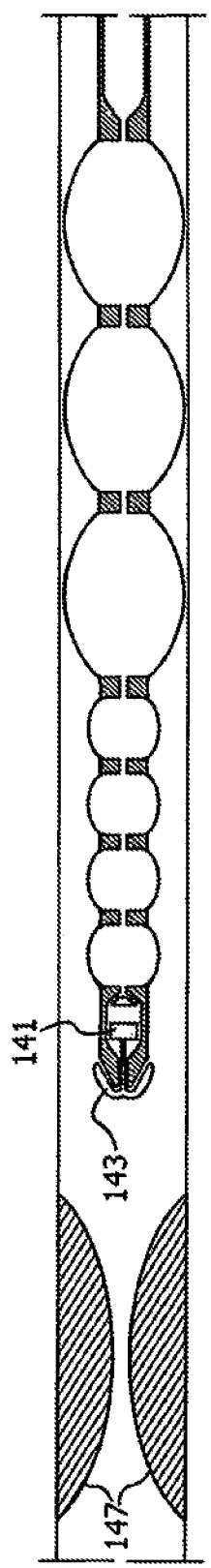
FIG. 14 illustrates an embodiment in which a turbine head is fitted to the front of the device, for burrowing its way through obstructions encountered.

Reference is now made to FIG. 14 which illustrates schematically a further preferred embodiment of the present invention, in which a drilling head 143, such as a turbine or propeller, is fitted to the front of the device, such that it can burrow its way through obstructions 147 encountered during its progress down the passageway. The head is preferably hydraulically powered with the power preferably coming from a paddle 141 or similar, driven by the inflating fluid, or from another external hydraulic source. Alternatively and preferably, electric power can be used, which can preferably come from a battery. Alternatively and preferably, the head can be powered from a rotating guide wire inserted through the center bore of the device.

FIGS. 13A to 13D and FIG. 14 describe the incorporation of various tip embodiments for enabling a self-propelled locomotion device of the present invention using serial chambers with automatic inflation sequencing, to force its way through partial blockages encountered in its path. However, it is to be understood that such tip embodiments as described in the embodiments of 13A to 13D and FIG. 14, and the benefits arising therefrom, can also be advantageously incorporated in any of the prior art inflatable chamber self-propelling devices, and the present invention is meant to include such embodiments also.

Figure 15A:
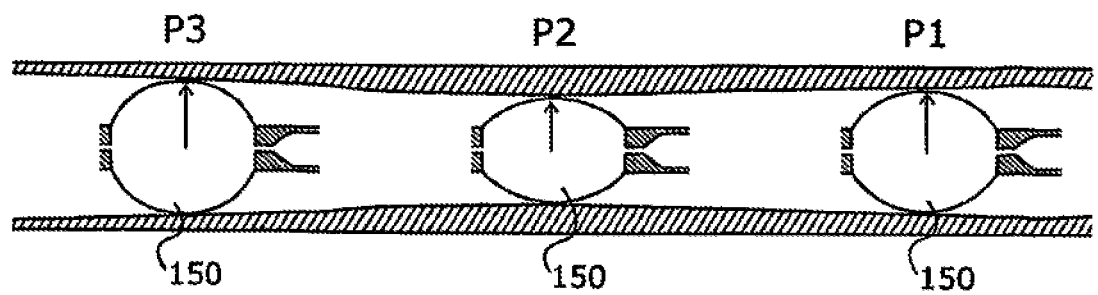
FIGS. 15A to 15B illustrate embodiments of the present invention, in which the device is utilized to determine parameters relating to the walls of a passageway negotiated by the device, such as internal diameter, and wall compliance.
Figure 15B:
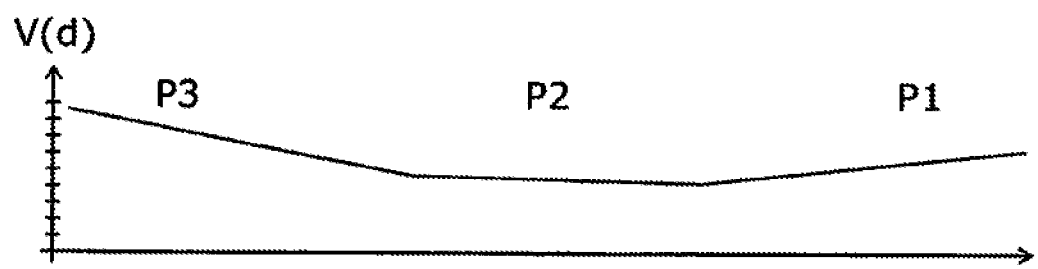

Reference is now made to FIGS. 15A and 15B, which illustrate schematically further preferred embodiments of the present invention, in which the device is utilized to determine a number of parameters relating to the walls of the passageway through which the device passes. In particular, the device is able to provide information regarding the passageway internal diameter, and the compliance of the passageway walls. The device and this method of operating it is thus particularly useful for profiling the condition of a subject's blood vessels or any other passageway at remote locations in his/her body. The device, according to this embodiment, requires the addition of a pressure monitor at the fluid input, and of a flow meter to determine the volume of inflation fluid required to fill the balloons of the device.

FIG. 15A illustrates a balloon, in this exemplary case, the proximal balloon 150, of the device of the present embodiment, at three different preferred locations along the length of a passageway, which, for the purposes of illustrating this preferred embodiment, will be regarded as a blood vessel. The blood vessel is shown having varying wall thicknesses, and hence a varying internal diameter. At point P3, the blood vessel inner diameter is large, at point P1 it is intermediate, and at point P2, it is a minimum. Correspondingly, the volume of fluid used to inflate the proximal balloon 150 is larger at point P3, less at point P1 and least at point P2. Measurement of the volumes required for inflation enables the blood vessel internal diameter to be determined at each cyclical point of the progress of the device through the vessel, once an initial calibration process has been performed to relate balloon volume to blood vessel diameter.

Continuous monitoring of the flow of inflation fluid during sequential filling of the balloons of the device enables a determination to be made of which balloon is being filled as a function of time, since there is a noticeable pressure change as each successive balloon begins to fill up, and monitoring these pressure changes allows the balloon being filled to be determined. It is thus possible to relate continuous volume and pressure measurements as a function of time, to the particular balloon being filled at any time. Since the filling volume is related to the blood vessel internal diameter, it is thus possible to obtain an estimation of this internal diameter at each point along the length of the device. This can be repeated at different positions of the device as it progresses along the vessel, such that a complete diameter profile of the blood vessel may be obtained. This is illustrated in FIG. 15B, which is a schematic graph showing a plot of the inflation volume V, as determined from the flow rate into the device, as a function of position along the device, which itself is determined from the pressure changes noted as a function of time. Since each inflated balloon volume is a function of the vessel diameter, d, the ordinate is designated V(d). As is seen from the graph, a correlation is shown between the inflation volume of each balloon and the vessel diameter at each point P1, P2, P3.

However, in addition to the use of the filling pressure to ascertain which balloon is currently being filled, this pressure can also be used in order to provide information about the compliance or rigidity of the vessel walls at points along its length. The position is known from the knowledge of which of the balloons is being filled at the time the pressure is measured, as explained above for the volume measurement. The vessel diameter at each point is also known from the method of FIG. 15B. There is a correlation between the vessel compliance, which is to be determined, and the pressure build-up and flow rate which can be measured, and hence the vessel wall compliance can be deduced from the corresponding time history of the pressure build-up and flow rate. Characterizing and calibrating measurements must first be performed in order to implement this correlation.

Figure 16:
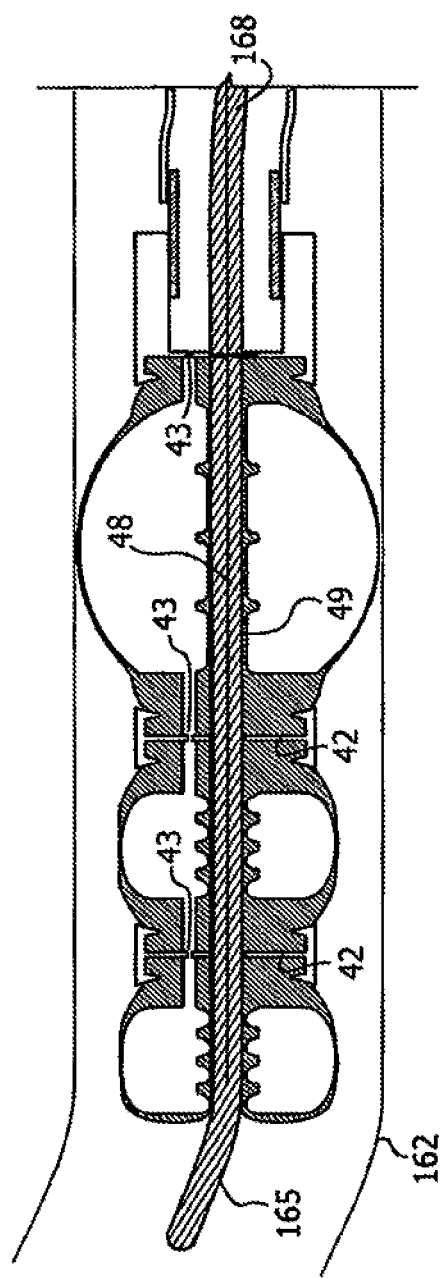
FIG. 16 illustrates schematically an embodiment in which the device is used in a novel steering system in coordination with an internal steerable guide wire, the device being propelled on the guide wire or the outer walls of the passageway.

Reference is now made to FIG. 16, which illustrates schematically a further preferred embodiment of the present invention, in which the device is used as a novel steering system in coordination with an internal pre-bent guide wire. In the prior art, steerable internal guide wires are generally used alone for negotiating curved passageways in the subject's body. However, such a steerable guide wire, in which the tip can be bent in the direction of a curve in the passageway being traversed, has the disadvantages that the tip can cause injury to the tissue of the internal wall of the passageway as it negotiates its way through the passageway, as can the trailing guide wire on curves in the passageway.

According to this preferred embodiment of the present invention, the steerable guide wire 168 is used as an internal member of the inflatable device as shown in the embodiments of FIGS. 4A-4B, or in the embodiments of FIGS. 12A-12B, where the inflatable device propels itself forward on the internal guide wire. In FIG. 16, the configuration of FIGS. 4A-4B is used to illustrate this embodiment. The steerable guide wire 168 is kept retracted within the crawling device as it moves forward, except when a curve 162 in the subject's passageway is to be negotiated, or a Y-junction is reached when the tip has to be directed to one branch or the other, in either of which cases the steerable tip 165 of the guide wire is allowed to protrude by a small distance from the front end in order to direct the front end of the device at the bifurcation. The small protrusion length prevents the tip from damaging the passageway wall because of the protection of the front balloon surrounding the guide wire tip and keeping it centrally located in the passageway. Alternatively and preferably, the steerable guide wire tip can be left just inside the tip of the device, without protruding at all, and steered from within, such that it directs the tip of the device round the curve without becoming exposed at all outside of the device. Progress through the lumen is thus primarily made by the tip of the inflatable device rather than the tip of a guide wire, thereby increasing the safety of use.

In the embodiments of the present invention using a central guide wire, such as are described in FIGS. 4A-4B and 12A-12B, the guide wire or central tube is generally inserted right to the end of the passage to be negotiated, and the device is allowed to crawl along it. However, there may be difficulties in inserting the guide wire all the way to its target, and in the process, the walls may be damaged by the tip, or by friction from the trailing guide wire, or dangerous plaque may be dislodged unintentionally. According to a further preferred embodiment of the present invention, a method of use of the device is provided whereby the internal guide wire is first inserted a short distance into the passageway to be traversed, typically of the order of 5 cm for passage down a blood vessel, is held in place externally, and the inflatable device is allowed to crawl along the passageway, as described in the embodiment of FIGS. 4A-4B, towards the tip of the guide wire. When the inflatable device has progressed sufficiently so that the steerable tip of the guide wire is preferably just enclosed within the device, the device is locked against the passage walls, and the guide wire is pushed forward a further short distance into the passage, and again held in place externally. The inflated device is then deflated to free it from the passage walls, and is then allowed to crawl forward until it again covers the exposed portion of the guide wire. This process is repeated until the guide wire reaches its target point. By this means, the guide wire is advanced within the passageway largely protected by the surrounding inflatable device, such that the likelihood of damage to the tissues of the passageway is greatly reduced.

As an alternative to the device climbing the walls of the passage, and anchoring itself on the walls as the guide wire is advanced, this method can also be used with the embodiment described in FIGS. 12A-12B, in which the device climbs along the internal guide wire itself, without applying pressure on the walls. In this case, the guide wire is pushed forward when the device is deflated without it being anchored, with the trailing inflation tube providing the small amount of resistance to hold the device in place while the guide wire is being advanced. Once the guide wire has been advanced a small distance, it is held in place externally, while the device crawls along it until has covered that small distance, at which point it releases itself from the guide wire, enabling the guide wire to be advanced another small distance, the whole process repeating itself until the target is reached.

It is appreciated by persons skilled in the art that the present invention is not limited by what has been particularly shown and described hereinabove. Rather the scope of the present invention includes both combinations and sub combinations of various features described hereinabove as well as variations and modifications thereto which would occur to a person of skill in the art upon reading the above description and which are not in the prior art.

We claim:

1. A device for locomotion through a lumen, comprising:
a set of serially arranged inflatable chambers; and
a fluid source configured to supply fluid to said set of serially arranged inflatable chambers, such that said fluid inflates the chambers of said set of serially arranged inflatable chambers in a serial sequence, from a first end of said set to a second end of said set;
wherein at least one chamber of said set of serially arranged inflatable chambers comprises an outer skin having at least one longitudinal section of greater rigidity than other sections of said outer skin, such that when said at least one chamber inflates, a bend is generated in said set of serially arranged inflatable chambers, at said at least one chamber.

2. A device according to claim 1, wherein said at least one longitudinal section is a reinforced section of said outer skin.

3. A device according to claim 2, wherein said reinforced section of said outer skin comprises one or more reinforcing strips.

4. A device according to claim 2, wherein said reinforced section of said outer skin is less flexible than the rest of the outer skin, such that said reinforced section is unable to stretch in the same manner as the other regions of said inflatable chamber.

5. A device according to claim 1, further comprising at least one connecting passage configured to provide fluid communication between each pair of adjacent chambers in said set of serially arranged inflatable chambers.

6. A device according to claim 1, wherein at least one chamber of said set of serially arranged inflatable chambers is configured to expand axially when inflated.

7. A device according to claim 1, wherein at least two chambers of said set of serially arranged inflatable chambers are configured to expand radially when inflated.

8. A device according to claim 7, wherein said at least two chambers are adapted to grip a wall of said lumen upon expanding radially.

9. A device according to claim 1, wherein said set of serially arranged inflatable chambers is configured to deflate in a serial sequence, from said first end of said set to said second end of said set, when said fluid flows out of said set of serially arranged inflatable chambers.

10. A device according to claim 9, wherein said device is configured to move along said lumen as the chambers of said set of serially arranged inflatable chambers inflate and deflate sequentially.

11. A device according to claim 1, further comprising:
at least one tubular chamber disposed between said fluid source and said set of serially arranged inflatable chambers, said at least one tubular chamber being adapted to inflate radially so as to apply pressure to said lumen walls; and
a pressure operated valve configured to close when a predetermined pressure higher than the pressure required to inflate said set of serially arranged inflatable chambers is applied thereto, said pressure operated valve being disposed between said tubular chamber and said set of serially arranged inflatable chambers, such that said set of serially arranged inflatable chambers is isolated from pressure applied to inflate said at least one tubular chamber.

12. A device for locomotion through a lumen, comprising:
a set of serially arranged inflatable chambers; and
a fluid source configured to supply fluid to said set of serially arranged inflatable chambers, such that said fluid inflates the chambers of said set of serially arranged inflatable chambers in a serial sequence, from a first end of said set to a second end of said set;
wherein at least one chamber of said set of serially arranged inflatable chambers comprises an outer skin having at least one longitudinal section of greater rigidity than other sections of said outer skin, such that when said at least one chamber inflates, said set of serially arranged inflatable chambers is configured to transition to a bent state.

13. A device for locomotion through a lumen, comprising:
a set of serially arranged inflatable chambers; and
a fluid source configured to supply fluid to said set of serially arranged inflatable chambers, such that said fluid inflates the chambers of said set of serially arranged inflatable chambers in a serial sequence, from a first end of said set to a second end of said set;
wherein at least one chamber of said set of serially arranged inflatable chambers comprises an outer skin having at least one longitudinal section of greater rigidity than other sections of said outer skin, such that when said at least one chamber inflates, those parts of said set of serially arranged inflatable chambers on either side of said at least one chamber, realign to have differently aligned axes.

* * * * *